US010196342B2

(12) United States Patent
Batra et al.

(10) Patent No.: US 10,196,342 B2
(45) Date of Patent: *Feb. 5, 2019

(54) SYNTHESIS OF INTERMEDIATES FOR PRODUCING PROSTACYCLIN DERIVATIVES

(71) Applicant: United Therapeutics Corporation, Silver Spring, MD (US)

(72) Inventors: Hitesh Batra, Herndon, VA (US); Sudersan M. Tuladhar, Silver Spring, MD (US); David A. Walsh, Spotsylvania, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/439,189

(22) Filed: Feb. 22, 2017

(65) Prior Publication Data
US 2017/0158602 A1 Jun. 8, 2017

Related U.S. Application Data

(63) Continuation of application No. 14/887,298, filed on Oct. 19, 2015, now Pat. No. 9,593,061.

(60) Provisional application No. 62/066,009, filed on Oct. 20, 2014.

(51) Int. Cl.
| C07C 67/343 | (2006.01) |
| C07C 45/67  | (2006.01) |
| C07C 45/81  | (2006.01) |
| C07C 67/31  | (2006.01) |
| C07C 67/333 | (2006.01) |
| C07C 45/64  | (2006.01) |
| C07C 45/78  | (2006.01) |

(52) U.S. Cl.
CPC ............ C07C 67/343 (2013.01); C07C 45/64 (2013.01); C07C 45/67 (2013.01); C07C 45/78 (2013.01); C07C 45/81 (2013.01); C07C 67/31 (2013.01); C07C 67/333 (2013.01); C07C 2103/14 (2013.01)

(58) Field of Classification Search
CPC ..... C07C 2103/14; C07C 45/64; C07C 45/78; C07C 67/31; C07C 67/343; C07C 47/565; C07C 45/67; C07C 45/81; C07C 67/333; C07C 47/575; C07C 69/84; C07C 69/92
See application file for complete search history.

(56) References Cited

U.S. PATENT DOCUMENTS

| 4,306,075 A | 12/1981 | Aristoff |
| 4,306,076 A | 12/1981 | Nelson |
| 4,424,376 A | 1/1984 | Moniot et al. |
| 4,434,164 A | 2/1984 | Lombardino |
| 4,463,183 A | 7/1984 | Haslanger |
| 4,486,598 A | 12/1984 | Aristoff |
| 4,544,764 A | 10/1985 | Aristoff |
| 4,668,814 A | 5/1987 | Aristoff |
| 4,683,330 A | 7/1987 | Aristoff |
| 5,039,814 A | 8/1991 | Shuman et al. |
| 5,153,222 A | 10/1992 | Tadepalli et al. |
| 5,234,953 A | 8/1993 | Crow et al. |
| 5,466,713 A | 11/1995 | Blitstein-Willinger et al. |
| 5,506,265 A | 4/1996 | Blitstein-Willinger |
| 6,054,486 A | 4/2000 | Crow et al. |
| 6,441,245 B1 | 8/2002 | Moriarty et al. |
| 6,521,212 B1 | 2/2003 | Cloutier et al. |
| 6,528,688 B2 | 3/2003 | Moriarty et al. |
| 6,569,894 B1* | 5/2003 | Takaki ................. C07D 307/79 514/469 |
| 6,700,025 B2 | 3/2004 | Moriarty et al. |
| 6,706,283 B1 | 3/2004 | Appel et al. |
| 6,756,033 B2 | 6/2004 | Cloutier et al. |
| 6,765,117 B2 | 7/2004 | Moriarty et al. |
| 6,803,386 B2 | 10/2004 | Shorr et al. |
| 6,809,223 B2* | 10/2004 | Moriarty ................. C07C 39/17 568/337 |
| 6,933,385 B2 | 8/2005 | Westermann et al. |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 7,879,909 B2 | 2/2011 | Wade et al. |
| 7,999,007 B2 | 8/2011 | Jeffs et al. |
| 8,232,316 B2 | 7/2012 | Phares et al. |
| 8,242,305 B2 | 8/2012 | Batra |
| 8,252,839 B2 | 8/2012 | Phares et al. |

(Continued)

FOREIGN PATENT DOCUMENTS

| CA | 2 710 726 A1 | 1/2012 |
| CN | 101891596 A | 11/2010 |

(Continued)

OTHER PUBLICATIONS

Rincon et al. (Safe, Convenient ortho-Claisen Thermal Rearrangement Using a Flow Reactor, Organic Process Reasearch & Development, Amer. Chem. Soc. 15, pp. 1428-1432, published 2011).*
Dewer et al. (Claisen Rearrangement of Cinnamyl Phenyl Ether in Isotropic and Nematic Solvents and in a Clathrate, JACS, 96, 2, p. 460-465, 1974).*
Bruce et al. (Claisen Rearrangement of meta-Substituted Allyl Phenyl Ethers, J. C. S. Perkin 1, pp. 2677-2679, 1981).*
Davis et al. (Microwave-Mediated Claisen Rearrangement Followed by Phenol Oxidation: A Simple Route to Naturally Occurring 1,4-Benzoquinones. The First Syntheses of Verapliquinones A and B and Panicein A, Journal of Organic Chemistry, 70, pp. 4414-4422, published Apr. 2005) (Year: 2005).*

(Continued)

Primary Examiner — Yevgeny Valenrod
Assistant Examiner — Blaine G Doletski
(74) Attorney, Agent, or Firm — Foley & Lardner LLP

(57) ABSTRACT

The present disclosure provides regioselective methods for synthesizing intermediates useful in making prostacyclin derivatives, such as treprostinil.

12 Claims, No Drawings

(56) References Cited

U.S. PATENT DOCUMENTS

| | | | |
|---|---|---|---|
| 8,349,892 B2 | 1/2013 | Phares | |
| 8,350,079 B2 | 1/2013 | Walsh | |
| 8,410,169 B2 | 4/2013 | Phares et al. | |
| 8,461,393 B2 | 6/2013 | Sharma | |
| 8,481,782 B2 | 7/2013 | Batra et al. | |
| 8,497,393 B2 | 7/2013 | Batra et al. | |
| 8,536,363 B2 | 9/2013 | Phares et al. | |
| 8,563,614 B2 | 10/2013 | Wade et al. | |
| 8,609,728 B2 | 12/2013 | Rothblatt et al. | |
| 8,653,137 B2 | 2/2014 | Jeffs et al. | |
| 8,658,694 B2 | 2/2014 | Jeffs et al. | |
| 8,765,813 B2 | 7/2014 | Wade et al. | |
| 8,940,930 B2 | 1/2015 | Batra et al. | |
| 9,029,607 B2 | 5/2015 | McGowan et al. | |
| 9,050,311 B2 | 6/2015 | Phares et al. | |
| 9,593,061 B2 * | 3/2017 | Batra | C07C 45/67 |
| 2001/0038855 A1 | 11/2001 | Desjardin et al. | |
| 2001/0056095 A1 | 12/2001 | Mylari | |
| 2002/0173672 A1 | 11/2002 | Moriarty et al. | |
| 2004/0176645 A1 | 9/2004 | Moriarty et al. | |
| 2005/0085540 A1 | 4/2005 | Phares et al. | |
| 2005/0101608 A1 | 5/2005 | Santel | |
| 2005/0165111 A1 | 7/2005 | Wade et al. | |
| 2005/0282901 A1 | 12/2005 | Phares et al. | |
| 2005/0282903 A1 | 12/2005 | Wade et al. | |
| 2006/0217574 A1 * | 9/2006 | Enokida | C07C 315/04 568/33 |
| 2007/0078095 A1 | 4/2007 | Phares et al. | |
| 2007/0078182 A1 | 4/2007 | Phares et al. | |
| 2007/0082948 A1 | 4/2007 | Phares et al. | |
| 2008/0200449 A1 | 8/2008 | Olschewski et al. | |
| 2008/0249167 A1 | 10/2008 | Phares et al. | |
| 2008/0280986 A1 | 11/2008 | Wade et al. | |
| 2009/0036465 A1 | 2/2009 | Roscigno et al. | |
| 2009/0124697 A1 | 5/2009 | Cloutier et al. | |
| 2009/0163738 A1 | 6/2009 | Batra et al. | |
| 2009/0281189 A1 | 11/2009 | Walsh | |
| 2010/0076083 A1 | 3/2010 | Olschewski | |
| 2010/0282622 A1 | 11/2010 | Phares | |
| 2011/0092599 A1 | 4/2011 | Wade et al. | |
| 2011/0118213 A1 | 5/2011 | Phares et al. | |
| 2011/0144204 A1 | 6/2011 | Jeffs et al. | |
| 2011/0224236 A1 | 9/2011 | Rothblatt et al. | |
| 2011/0319641 A1 | 12/2011 | Batra et al. | |
| 2012/0004307 A1 | 1/2012 | Wade et al. | |
| 2012/0010159 A1 | 1/2012 | Rothblatt et al. | |
| 2012/0190888 A1 | 7/2012 | Batra et al. | |
| 2012/0197041 A1 | 8/2012 | Batra et al. | |
| 2012/0216801 A1 | 8/2012 | Olschewski et al. | |
| 2012/0226076 A1 | 9/2012 | Sharma | |
| 2013/0184295 A1 | 7/2013 | Sprague et al. | |
| 2013/0211145 A1 | 8/2013 | McGowan et al. | |
| 2014/0024856 A1 | 1/2014 | Giust et al. | |
| 2014/0275262 A1 | 9/2014 | Phares et al. | |
| 2014/0275616 A1 | 9/2014 | Batra et al. | |
| 2014/0323567 A1 | 10/2014 | Laing | |
| 2015/0025255 A1 | 1/2015 | Yiannikouros et al. | |

FOREIGN PATENT DOCUMENTS

| | | |
|---|---|---|
| CN | 101891715 A | 11/2010 |
| EP | 0 004 335 A2 | 10/1979 |
| EP | 0 087 237 B1 | 5/1986 |
| EP | 0 175 450 B1 | 3/1989 |
| EP | 0 159 784 B1 | 6/1989 |
| EP | 0 496 548 A1 | 7/1992 |
| JP | 56-122328 A | 9/1981 |
| JP | 59-044340 A | 3/1984 |
| WO | WO 98/18452 A1 | 5/1988 |
| WO | WO 98/39337 A1 | 9/1998 |
| WO | WO 99/21830 A1 | 5/1999 |
| WO | WO 00/57701 A1 | 10/2000 |
| WO | WO 02/053517 A2 | 7/2002 |
| WO | WO2003/047584 * | 6/2003 |
| WO | WO 03/070163 A2 | 8/2003 |
| WO | WO 2005/007081 A2 | 1/2005 |
| WO | WO 2007/134292 A2 | 11/2007 |
| WO | WO 2008/100977 A2 | 8/2008 |
| WO | WO 2009/117095 A1 | 9/2009 |
| WO | WO2011153363 * | 12/2011 |
| WO | WO 2012/009816 A1 | 1/2012 |
| WO | WO2012009816 * | 1/2012 |

OTHER PUBLICATIONS

Harlan et al. (A Kinetic Study of the ortho-Claisen Rearrangement, J. Am. Chem. Soc., 80, pp. 3277-3285, published Jul. 1958) (Year: 1958).*

Alexander et al., "The Synthesis of Benzindene Prostacyclin Analogs as Potential Antiulcer Agents," Prostaglandins, 1986, 32(5):647-653.

Aristoff et al., "Synthesis and Structure-Activity Relationship of Novel Stable Prostacyclin Analogs," Advances in Prostaglandin, Thromboxane, and Leukotriene Research, Samuelsson et al., .Eds., 1983, 11:267-274.

Aristoff et al,, "Synthesis of Benzopyran Prostaglandins, Potent Stable Prostacyclin Analogs, Via an intramolecular Mistunobu Reaction," Tetrahedron Letters, 1984, 25(36):3955-3958.

Aristoff et al., "Total Synthesis of a Novel Antiulcer Agent via a Modification of the Intramolecular Wadsworth-Emons-Wittig Reaction," J. Am. Chem. Soc., 1985, 107:7967-7974.

Batra et al., "Crystallization Process Development for a Stable Polymorph of Treprostinil Diethanolamine (UT-15C) by Seeding," Organic Process Research & Development, 2009, 13:242-249.

Belch et al., "Randomized, Double-Blind, Placebo-Controlled Study Evaluating the Efficacy and Safety of AS-013, a Prostaglandin E1 Prodrug, in Patients with Intermittent Claudication," Circulation, May 6, 1997, 95(9):2298-2302.

Bighley et al., "Salt Forms of Drugs and Absorption," Encyclopedia of Pharmaceutical Technology, Swarbrick et al., Eds., 1995, 13:453-499.

Bowman et al., "Approaches for Scale-Up of Microwave-Promoted Reactions," Organic Process Research & Development 2008, 12 (1):41-57.

Chemburkar et al., "Dealing with the Impact of Ritonavir Polymorphs on the Late Stages of Bulk Drug Process Development," Organic Process Research & Development, 2000, 4:413-417.

Chung et al., "Promoters for the (Alkyne)hexacarbonyldicobalt-Based Cyclopentenone Synthesis," Organometallics, 1993, 12:220-223.

Clark et al., "High-Performance Liquid Chromatographic Method for Determining the Enantiomeric Purity of a Benzindene Prostaglandin by a Diastereomeric Separation," Journal of Chromatography, 1987, 408:275-283.

Comins et al., "Ortho Metalation Directed by α-Amino Alkoxides," J. Org. Chem., 1984, 49:1078-1083.

Comins et al., "Ortho Substitution of M-Anisaldehyde via α-Amino Alkoxide Directed Lithiation," J. Org. Chem., 1989, 54:3730-3732.

Corey et al. "Novel Electronic Effects of Remote Substituents on the Oxazaborolidine-Catalyzed Enantioselective Reduction of Ketones," Tetrahedron Letters, 1995, 36(50):9153-9156.

De La Hoz et al., "Microwaves in organic synthesis. Thermal and non-thermal microwave effects," Chem. Soc. Rev., 2005, 34:164-178.

Giguere et al., "Application of Commercial Microwave Ovens to Organic Synthesis," Tetrahedron Letters, 1986, 27(41):4945-4948.

Greene, TW, et al., "Protecting Groups," 1991, 1-11.

Hardinger et al., "Triply-Convergent Syntheses of Two Homochiral Arene-Fused Prostacyclin Analogs Related to U68,215," Bioorganic & Medicinal Chemistry Letters, 1991, 1(1):79-82.

Hicks et al., "A Practical Titanium-Catalyzed Synthesis of Bicyclic Cyclopentenones and Allylic Amines," J. Org. Chem., 1996, 61:2713-2718.

Jeong et al., "Catalytic Version of the Intramolecular Pauson-Khand Reaction," J. Am. Chem. Soc., 1994, 116:3159-3160.

(56) References Cited

OTHER PUBLICATIONS

Khand et al., "Organocobalt Complexes. Part II. Reaction of Acetylenehexacarbonyl-dicobalt Complexes, $(R^1C_2R^2)Co_2(CO)_6$, with Norbornene and its Derivatives," J. Chem. Soc., J.C.S. Perkin I., 1973, 977-981.
Martin et al., "General Methods for Alkaloid Synthesis. Total Synthesis of Racemic Lycoramine," J. Org. Chem., 1982, 47:1513-1518.
Mathre et al., "A Practical Enantioselective Synthesis of α, α-Diaryl-2-pyrrolidinemethanol. Preparation and Chemistry of the Corresponding Oxazaborolidines," J. Org. Chem., 1991, 56:751-762.
Mmutlane et al., "The synthesis of ventiloquinone L, the monomer of cardinalin 3," Org. Biomol. Chem., 2004, 2:2461-2470.
Moriarty et al., "The Intramolecular Asymmetric Pauson-Khand Cyclization as a Novel and General Stereoselective Route to Benzindene Prostacyclins: Synthesis of UT-15 (Treprostinil)," *J. Org. Chem.* 2004, 69, 1890-1902.
Mullin, John W., "Crystallization and Precipitation," Ullmann's Encyclopedia of Industrial Chemistry, 2002, 1-51.
Mulzer et al., "Asymmetric Synthesis of Carbacyclin Precursors by Pauson-Khand Cyclization," Liebigs Ann. Chem., 1988, 891-897.
Nelson, Norman A., "Prostaglandin Nomenclature," J. Med. Chem., Sep. 1974, 17(9):911-918.
Nicolaou et. al., "Solid- and Solution-Phase Synthesis of Vancomycin and Vancomycin Analogues with Activity against Vancomycin-Resistant Bacteria," Chem. Eur. J., 2001, 7(17):3798-3823.
Pagenkopf et al., "Photochemical Promotion of the Intramolecular Pauson-Khand Reaction. A New Experimental Protocol for Cobalt-Catalyzed [2+2+1] Cycloadditions," J. Am. Chem. Soc., 1996, 118:2285-2286.
Pagenkopf, Brian L., "Substrate and Reagent Control of Diastereoselectivity in Transition Metal-Mediated Process: Development of a Catalytic Photo Promoted Pauson-Khand Reaction," Diss. Abstr. Int., 57(12):7535, 1977, Abstract.
Pansegrau et al., "The Oxazoline-Benzyne Route to 1,2,3-Trisubstituted Benzenes. Tandem Addition of Organolithiums, Organocuprates, and α-Lithionitriles to Benzynes," J. Am. Chem. Soc., 1988, 110:7178-7184.
Patterson et al., "Acute Hemodynamic Effects of the Prostacyclin Analog 15AU81 in Severe Congestive Heart Failure," Am. J. Cardio., 1995, 75:26-A-33A.
Paul et al.; "Expanding the regioselective enzymatic repertoire: oxidative mono-cleavage of dialkenes catalyzed by *Trametes hirsute*," Chemical Communications, 2012, 48(27):3303-3305.
Pauson, Peter L., "The Khand Reaction," Tetrahedron, 1985, 41(24):5855-5860.
Polshettiwar et al., "Microwave-Assisted Organic Synthesis and Transformations using Benign Reaction Media," Accounts of Chemical Research, May 2008, 41(5):629-639.
Rincon et al., "Safe, Convenient Orth-Claisen Thermal Rearrangement Using a Flow Reactor," Organic Process & Development, American Chemical Society, 2011, 15:1428-1432.
Rowley et al., "Application of the Pauson-Khand reaction to the synthesis of pentalenic acid," Journal of Organometallic Chemistry, 1991, 413:C5-C9.
Satoh et al., "Palladium-Catalyzed Etherification of Allyl Alcohols Using Phenols in the Presence of Titanium(IV) Isopropoxide," J. Org. Chem., 1997, 62, 4877-4879.
Sauks et al., "A Continuous-Flow Microwave Reactor for Conducting High-Temperature and High-Pressure Chemical Reactions," Organic Process Research & Development, 2014, 18(11):1310-1314.
Schore, Neil E., "Transition-Metal-Mediated Cycloaddition Reactions of Alkynes in Organic Synthesis," Chem. Rev., 1988, 88:1081-1119.
Shambayati et al., "N-Oxide Promjoted Pauson-Khand Cyclizations at Room Temperature," Tetrahedron Letters, 1990, 31(37):5289-5292.
Simonneau et al., "Continuous Subcutaneous Infusion of Treprostinil, a Prostacyclin Analogue, in Patients with Pulmonary Arterial Hypertension," Am. J. Respir. Crit. Care Med., 2002, 165:800-804.
Snell et al., "Investigating the Effect of Impurities on Macromolecule Crystal Growth in Microgravity," Crystal Growth & Design, 2001, 1(2):151-158.
Sorbera et al. "UT-15. Treatment of Pulmonary Hypertension Treatment of Peripheral Vascular Disease," *Drug of the Future*, 2001, 26(4), 364-374.
Strauss et al., "Invited Review. Developments in Microwave-assisted Organic Chemistry," Aust. J. Chem., 1995, 48(10):1665-1692.
Takano et al., "Enantiodivergent Synthesis of Both Enantiomers of Sulcatol and Matsutake Alcohol from (R)-Epichlorohydrin," Chemistry Letters, 1987, 2017-2020.
Viedma, Cristobal, "Selective Chiral Symmetry Breaking during Crystallization: Parity Violation of Cryptochiral Environment in Control?" Crystal Growth & Design, 2007, 7(3):553-556.
Whittle et al., "Antithrombotic Assessment and Clinical Potential of Prostacyclin Analogues," Progress in Medicinal Chemistry, Ellis et al. Eds., 1984, Chapter 6, vol. 21, 238-279.
Wuts et al., Greene's Protecting Groups in Organic Synthesis, John Wiley & Sons, Inc. 2007, 4th edition; pp. 367-430, 543-544.
Zhang et al., "A Nickel(0)-Catalyzed Process for the Transformation of Enynes to Bicyclic Cyclopentenones," J. Org. Chem., 1996, 61:4498-4499.

* cited by examiner

SYNTHESIS OF INTERMEDIATES FOR PRODUCING PROSTACYCLIN DERIVATIVES

RELATED APPLICATIONS

The present application is a Continuation of U.S. application Ser. No. 14/887,298, filed Oct. 19, 2015, which claims priority to U.S. provisional application No. 62/066,009 filed Oct. 20, 2014, which is incorporated herein by reference in its entirety.

FIELD

The present application generally relates to chemical synthetic methods and in particular, to synthesis of aldehyde compounds, which may be useful in preparation of pharmaceutically active prostacyclins, such as treprostinil.

SUMMARY

A method of producing a compound of formula 3:

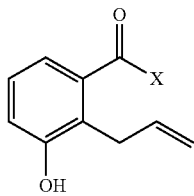

comprising heating a solution comprising a compound of formula 2:

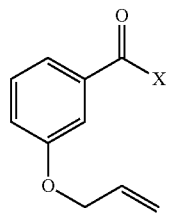

and an organic solvent, and wherein X is hydrogen, an alkoxy group or $OR^2$, wherein $R^2$ is unsubstituted or substituted aryl, or unsubstituted or substituted benzyl. The heating can comprise irradiating the solution with microwave radiation.

DETAILED DESCRIPTION

Unless otherwise specified, "a" or "an" means "one or more."

The term "aryl," alone or in combination with another radical, means a carbocyclic aromatic system containing one, two, or three rings wherein such rings may be attached together in a pendent manner or may be fused. The term "aryl" embraces aromatic radicals including, but not limited to, phenyl, naphthyl, tetrahydronaphthyl, indyl, and biphenyl. A substituted aryl group may be optionally substituted at one or more positions with one or more substituents, which may be independently selected from the group consisting of —$NO_2$, —CN, halogen (e.g., —F, —Cl, —Br or —I), ($C_1$-$C_3$)alkyl, halo($C_1$-$C_3$)alkyl, ($C_1$-$C_3$)alkoxy, and halo($C_1$-$C_3$)alkoxy.

Prostacyclin derivatives are useful pharmaceutical compounds possessing activities, such as platelet aggregation inhibition, gastric secretion reduction, lesion inhibition, and bronchodilation.

Treprostinil, the active ingredient in Remodulin®, Tyvaso®, and Orenitram™, was first described in U.S. Pat. No. 4,306,075. Methods of making treprostinil and other prostacyclin derivatives are described, for example, in Moriarty, et al., *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, and 8,940,930; U.S. Published Patent Application Nos. 2012-0197041, 2013-0211145, 2014-0024856, 2015-0025255; and PCT Publication No. WO 2012/009816.

Various uses and/ or various forms of treprostinil are disclosed, for examples, in U.S. Pat. Nos. 5,153,222, 5,234,953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, U.S. Published Patent Application Nos. 2009-0036465, 2008-0200449, 2010-0076083, 2012-0216801, 2008-0280986, 2009-0124697, 2014-0275616, 2014-0275262, 2013-0184295, 2014-0323567, PCT Publication No. WO00/57701.

Treprostinil, also known as UT-15, LRX-15, 15AU81, UNIPROST™, BW A15AU;

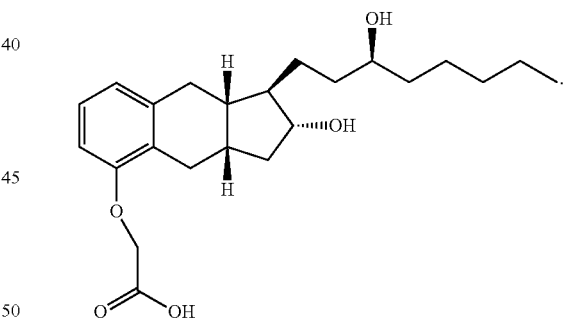

and U-62,840 has the following chemical formula:

The present inventors developed novel methods for synthesizing aldehyde compounds. These aldehyde compounds can be intermediates in processes for producing treprostinil and other prostacyclin derivatives or pharmaceutically acceptable salts or esters thereof, such as the processes disclosed in Moriarty, et al. *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 7,417,070, 8,461,393, 8,481,782, 8,242,305, and 8,497,393, U.S. Published Patent Application Nos. 2012-0190888 and 2012-0197041, PCT Publication No. WO2012/009816.

In one embodiment, the present disclosure provides a method of producing a compound of formula 3:

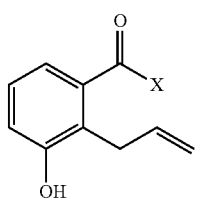

by heating a solution comprising a compound of formula 2

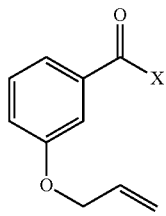

and an organic solvent. In some embodiments, the heating comprises irradiating said solution with a microwave radiation. In the above formulae, X may be hydrogen, an alkoxy group or $OR_2$, where unsubstituted or substituted aryl, or unsubstituted or substituted benzyl.

Use of microwave radiation in chemistry is known to those skilled in the art. See e.g. Polshettiwar, V.; et al Accounts of Chemical Research 2008, 41 (5), 629-639; Bowman, M. D.; Organic Process Research & Development 2007, 12 (1), 41-57; Sauks, J. M. et al., Organic Process Research & Development 2014, 18(11):1310-1314; *Microwaves in organic synthesis*, Andre Loupy (ed), Wiley-VCH, Weinheim, 2006; *Microwaves in organic synthesis. Thermal and non-thermal microwave effects*, Antonio de la Hoz, Angel Diaz-Ortiz, Andres Moreno, Chem. Soc. Rev., 2005, 164-178; *Developments in Microwave-assisted Organic Chemistry*. C. Strauss, R. Trainor. Aust. J. Chem., 48 1665 (1995); *Microwaves in Organic and Medicinal Chemistry*, 2nd, Completely Revised and Enlarged Edition, Wiley-VCH, Weinheim, 2012.

In certain embodiments, the heating with the microwave radiation may be performed at a temperature ranging from 150° C. to 200° C. or from 175° C. to 195° C., such as within a range of 182-185° C.

The heating with the microwave radiation may performed for 1 hour to 30 hours, from 2 hours to 25 hours, from 2 hours to 20 hours, from 2 hours to 15 hours, from 3 hours to 14 hours, any value or any subrange within these ranges. In some embodiments, the reaction times may be significantly lower compared to the ones of prior art methods.

Use of microwave radiation or conventional heating to heat a solution comprising the compound of formula 2 may result in producing the isomer of the compound of formula 3, a compound of formula 4:

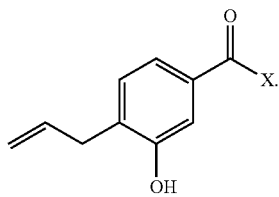

Selection of appropriate solvents can result in separating the compound of formula 3 from the compound of formula 4 through a selective crystallization of one of the isomers. Appropriate solvents include, but are not limited to, 1,2-dichlorobenzene or tetrahydronaphtalene. This means that one of the isomers, e.g. the compound of formula 3 may crystallize, while the other of the isomers, e.g. the compound of formula 3, would remain dissolved in the solvent. In some embodiments, the methods described herein allow producing a high-purity batch of the compound of formula 3 having a purity of at least 95% by weight of the composition, , at least 96% or at least 97%, at least 98%, at least 98.5%, at least 99%, at least 99.1%, at least 99.2%, at least 99.3%, at least 99.4%, at least 99.5%, at least 99.6%, least 99.7%, at least 99.8%, or at least 99.9% by weight of the composition.

Selective crystallization allows for production high-purity batches of the compound of formula 3 without performing column chromatography purifications, which may save manpower, large volumes of solvents, and lost product.

In some embodiments, the methods described herein permit production of the compound of formula 3 in large quantities, such as at least 10 g, at least 20 g, at least 30 g, at least 50 g, at least 80 g, at least 100 g, at least 150 g, at least 200 g, at least 250 g, at least 300 g, at least 400 g, at least 500 g, at least 800 g, at least 1000 g, at least 1200 g, at least 1500 g, at least 2000 g, at least 2500 g, at least 3000 g, at least 3500 g, at least 4000 g, at least 4500 g, at least 5000 g, at least 6000 g; at least 7000 g, at least 8000 g, at least 9000 g, or at least 10000 g.

In some embodiments, X may be hydrogen or an alkoxy group, which may be, for example, $C_1$-$C_8$ alkoxy group or $C_1$-$C_4$ alkoxy group, such as methoxy or ethoxy. The solvent in the solution comprising the compound of formula 2 may comprise, for example, at least one of triglyme, N-methylpyrrolidinone, tetradecane, tetrahydronaphtalene, Dowtherm A™, p-chlorophenol, 1,2-dichlorobenzene, and diphenyl ether. In some embodiments, the solvent in the solution comprising the compound of formula 2 may comprise, for example, at least one of 1,2-dichlorobenzene and tetrahydronaphtalene.

In some embodiments, X may be $OR_2$, where $R_2$ is $C_{1-4}$ alkyl, unsubstituted or substituted aryl, or unsubstituted or substituted benzyl. The $C_{1-4}$ alkyl can be methyl, ethyl, propyl, isopropyl, n-butyl, isobutyl, sec-butyl or tert-butyl. Non-limiting examples of X include $OCH_3$; $OCH_2CH_3$ and $OCH_2Ph$. The solvent in the solution comprising the compound of formula 2 may comprise, for example, at least one of triglyme, N-methylpyrrolidinone, tetradecane, tetrahydronaphtalene, Dowtherm A™ (a mixture of 26.5% diphenyl and 73.5% diphenyl oxide), p-chlorophenol, 1,2-dichlorobenzene and diphenyl ether. In some embodiments, the solvent in the solution comprising the compound of formula 2 may comprise, for example, at least one of 1,2-dichlorobenzene and tetrahydronaphtalene.

In some embodiments, the compound of formula 3 may be converted to a compound of formula 5

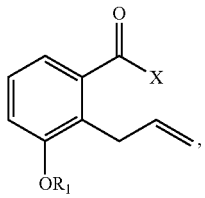

using O-alkylation, wherein $R_1$ is selected from (a) benzyl or substituted benzyl and (b) $CH_2COOR_4$, wherein $R_4$ is $C_{1-4}$ alkyl, such as methyl, ethyl, propyl, isopropyl, n-butyl, isobutyl, sec-butyl or tent-butyl. The purity of a batch of the compound of formula 5 may be as high as purity of the batch of the compound of formula 3. O-alkylation of phenol is known in the art, see e.g. P. G. M. Wuts and T. W. Greene, "Greene's Protecting Groups in Organic Synthesis", John Wiley & Sons, Inc. 2007, 4th edition; page 390; F. Martin and P. J. Garrison; J. Org. Chem., 1982, 47, 1513; T. Satoh, M. Ikeda, M. Miura and M. Nomura: J. Org. Chem., 1997, 62, 4877.

In some embodiments, when $R_1$ is hydrogen, O-alkylation may be performed by reacting the compound of formula 3 with benzyl halides, such as BnCl, BnBr or BnI. Such reaction may be performed in an alkaline solution, which may be, for example, an aqueous solution of $K_2CO_3$. Other O-alkylation conditions of phenol are known in the art, see e.g. P. G. M. Wuts and T. W. Greene, "Greene's Protecting Groups in Organic Synthesis," John Wiley & Sons, Inc., 2007, $4^{th}$ Edition, page 370.

A substituted benzyl group may be optionally substituted at one or more meta, ortho, or para positions with one or more substituents, which may be independently selected from the group consisting of $-NO_2$, $-CN$, halogen (e.g., $-F$, $-Cl$, $-Br$ or $-I$), $(C_1-C_3)$alkyl, halo$(C_1-C_3)$alkyl, $(C_1-C_3)$alkoxy, and halo$(C_1-C_3)$alkoxy.

In some embodiments, the compound of formula 5 may then converted to treprostinil or its pharmaceutically acceptable salt through a process comprising Pauson-Khand cyclization. Such processes are disclosed, for example, in U.S. Pat. Nos. 8,481,782, 6,700,025, 6,809,223, 6,441,245, 6,765,117, 6,528,688, and U.S. Published Patent Application Nos. 2012-0190888 and 2012-0197041.

In some embodiments, when X is $OR_2$, where $R_2$ is $C_{1-4}$ alkyl, the compound of formula 3 may be used for forming a compound of formula 11

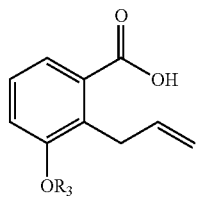

through O-alkylation and hydrolysis, wherein $R_3$ is $C_{1-4}$ alkyl or a phenolic protecting group. O-alkylation is known in the art, see e.g. P. G. M. Wuts and T. W. Greene, "Greene's Protecting Groups in Organic Synthesis", John Wiley & Sons, Inc. 2007, 4th edition; page 390; F. Martin and P. J. Garrison; J. Org. Chem., 1982, 47, 1513; T. Satoh, M. Ikeda, M. Miura and M. Nomura: J. Org. Chem., 1997, 62, 4877. Hydrolysis of esters is known in the art as well. In some embodiments, the selective hydrolysis may be performed using a bulky base, such as barium hydroxide, cesium hydroxide, or trialkyl ammonium hydroxide. In some embodiments, the trialkyl ammonium hydroxide can be tributyl ammonium hydroxide or trimethyl ammonium hydroxide. In some embodiments, a base for selective hydrolysis may be an alkali metal hydroxide. Although the use of bulky bases, such as barium hydroxide and cesium hydroxide, other alkali metal hydroxides, such as potassium hydroxide and sodium hydroxide may be used if they can provide selective hydrolysis of one of regioisomers. A base used in selective hydrolysis may selectively hydrolyze one (less hindered) isomer, and this may provide the advantage of separating the desired isomer in the present synthesis, see e.g. Scheme 2. Ester hydrolysis using various conditions are disclosed, for example, in P. G. M. Wuts and T. W. Greene, "Greene's Protecting Groups in Organic Synthesis", John Wiley & Sons, Inc. 2007, 4th edition; page 543-544.

As used herein, "a phenolic protecting group" is a modification that protects the hydroxyl group from participating in reactions that are occurring in other parts of the molecule. Suitable phenolic protecting groups are well known to those of ordinary skill in the art and include those found in P. G. M. Wuts and T. W. Greene, "Greene's Protecting Groups in Organic Synthesis", John Wiley & Sons, Inc. 2007, 4th edition; page 367-430, the entire teachings of which are incorporated herein by reference. Exemplary phenolic protecting groups include, but are not limited to, actetyl, benzoyl, benzyl, p-methoxyethoxymethyl, methoxymethyl, dimethoxytrityl, p-methoxybenzyl, trityl, silyl (e.g., trimethylsilyl (TMS), tert-butyldimethylsilyl (TBMDS), tert-butyldimethylsilyloxymethyl (TOM) or triisopropylsilyl (TIPS), tetrahydropyranyl (THP), methyl and ethoxyethyl (EE).

In some embodiments, the compound of formula 11 may then converted to treprostinil or its pharmaceutically acceptable salt through a process comprising Pauson-Khand cyclization. Such processes are disclosed, for example, in U.S. Pat. Nos. 8,481,782, 6,700,025, 6,809,223, 6,441,245, 6,765,117, and 6,528,688 and U.S. Published Patent Application Nos. 2012-0190888 and 2012-0197041.

In some embodiments, the compound of formula 2 used for making the compound of formula 3 may be produced by allylating a compound of formula 1

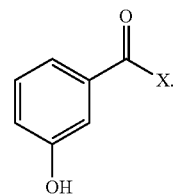

Allylation reactions are disclosed, for example, in By Nicolaou, K. C. et. al.; From Chemistry—A European Journal, 7(17), 3798-3823; 2001; Moriarty R. M. et. al. ; From PCT Int. Appl., 2002053517, 11 Jul. 2002; Mmutlane, Edwin M. et. al. From Organic & Biomolecular Chemistry, 2(17), 2461-2470; 2004; Paul, Caroline E. et. al.; From Chemical Communications (Cambridge, United Kingdom), 48(27), 3303-3305; 2012. In some embodiments, the disclosed methods may provide one or more of the following advantages: a) reduce reaction times; b) provide high purity batches of a desired isomer by using selective crystallization of the desired isomer depending on the solvents used; c) eliminate column chromatographic purifications and thereby, significantly save manpower and large volume of solvents; d) be scaled up to kilo-gram quantities; e) the compound of formula 3 may be used to synthesize various O-ethers, esters and acid functionalities, which may be useful synthons for the synthesis of prostacyclins, such as treprostinil. Embodiments described herein are further illustrated by, though in no way limited to, the following examples.

EXAMPLES

A protocol (Scheme 1) has been developed for the synthesis of 2-allyl-3-hydroxy benzaldehyde (3) via Claisen rearrangement of allyl-ether of 3-hydroxybenzaldehyde (2) using microwave. The allyl ether (2) is heated by irradiating microwaves in various solvents (see Table 1) app. at 180° C. for 7-12 hrs. The use of microwave enhances the rate of reaction and significantly may reduce the reaction times over conventional thermal rearrangement. Also, the desired isomer (3) crashes out as white to off-white solid leaving the non-desired aldehyde (regio-isomer) (4) in mother liquor.

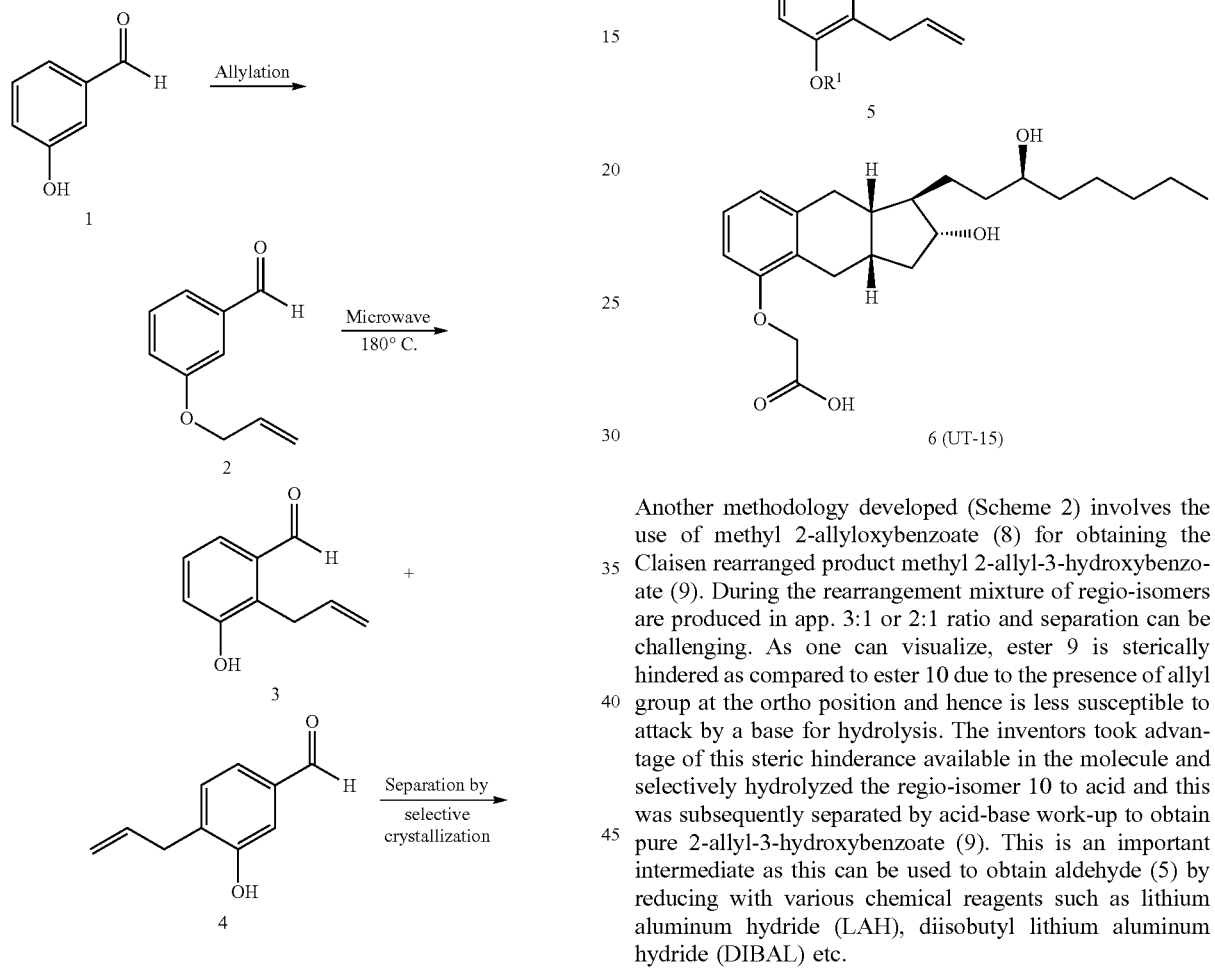

Another methodology developed (Scheme 2) involves the use of methyl 2-allyloxybenzoate (8) for obtaining the Claisen rearranged product methyl 2-allyl-3-hydroxybenzoate (9). During the rearrangement mixture of regio-isomers are produced in app. 3:1 or 2:1 ratio and separation can be challenging. As one can visualize, ester 9 is sterically hindered as compared to ester 10 due to the presence of allyl group at the ortho position and hence is less susceptible to attack by a base for hydrolysis. The inventors took advantage of this steric hinderance available in the molecule and selectively hydrolyzed the regio-isomer 10 to acid and this was subsequently separated by acid-base work-up to obtain pure 2-allyl-3-hydroxybenzoate (9). This is an important intermediate as this can be used to obtain aldehyde (5) by reducing with various chemical reagents such as lithium aluminum hydride (LAH), diisobutyl lithium aluminum hydride (DIBAL) etc.

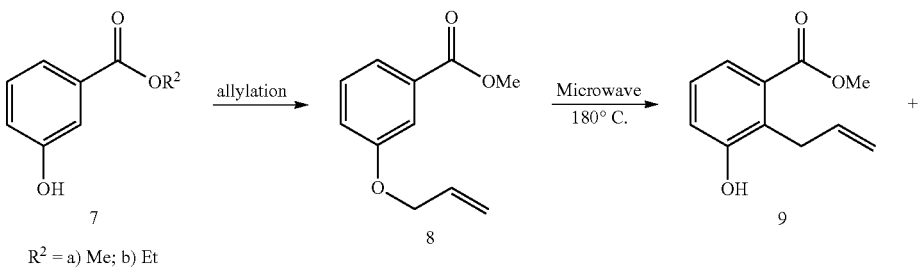

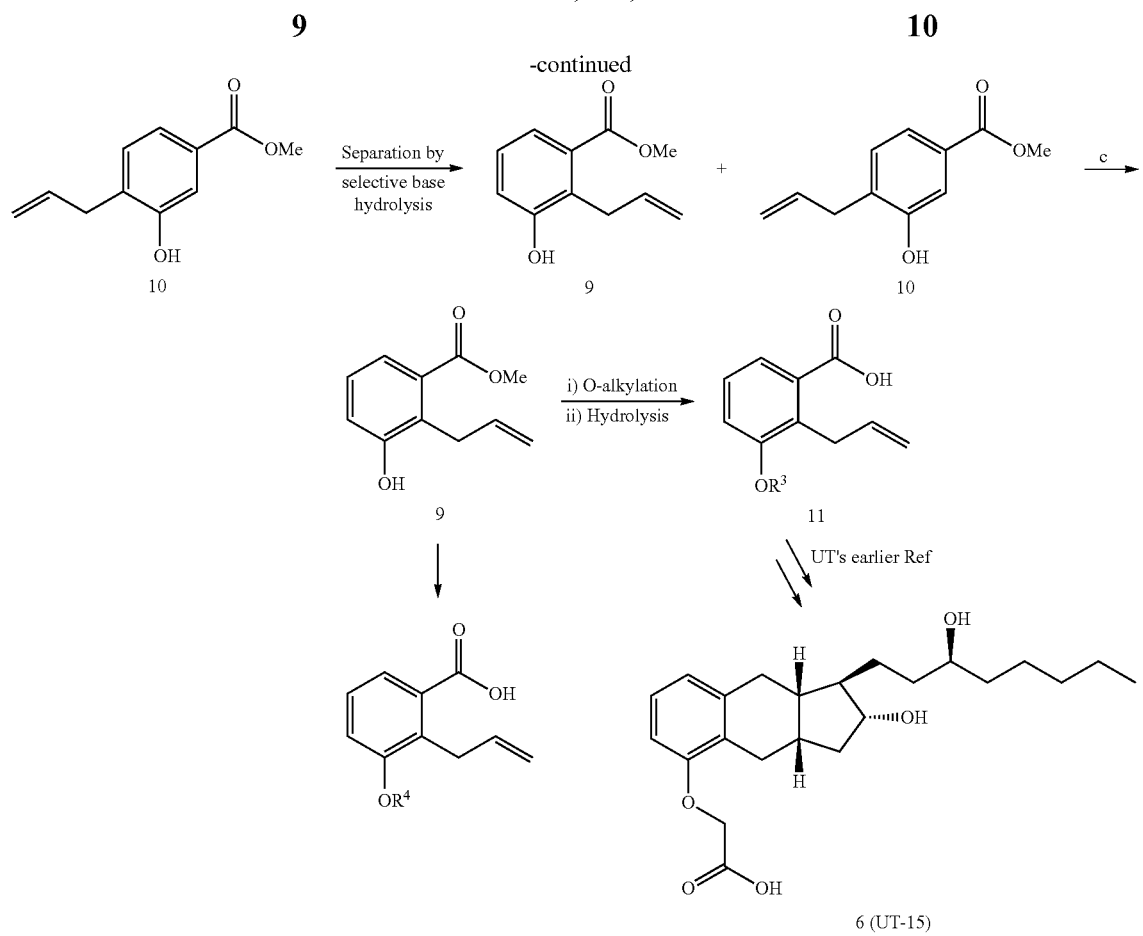

A brief overview of the experiments carried on Claisen rearrangement is given below in table 1.

Table 1: Study Results on Claisen Rearrangement (2→3)

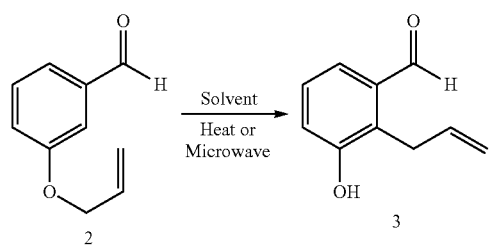

| S. No. | Lot # | Solvent | Amount | Temp. | Time |
|---|---|---|---|---|---|
| 1 | D-1057-087 | Triglyme | 1.0 g | 180-182° C. | 22 h |
| 2 | D-1057-088 | N-methyl pyrrolidinone | 1.0 g | 180-182° C. | 22 h |
| 3 | D-1057-089 | Carbitol | 1.0 g | 180-182° C. | 19 h |
| 4 | D-1057-090 | Tetradecane | 1.0 g | 190-192° C. | 19 h |
| 5 | D-1057-063 | Tetrahydro-naphthalene | 3.0 g | 180-182° C. | 11 h |
| 6 | D-1057-066 | Dowtherm A ™ (mixture of diphenyl 26.5% and diphenyl oxide 73.5%) | 1.0 g | 190-192° C. | 6 h |
| 7 | D-1057-064 D-1057-069 | Neat | 4.0 g 15.0 g | 180-182° C. | 30 min. |
| 8 | D-1057-144 | Para-cholorophenol | 1.0 g | 160-162° C. | 1 h |
| 9 | D-1057-145 | N-methyl pyrrolidinone | 1.0 g | 180-182° C. | 1 h |
| 10 | D-1057-147 | Tetrahydro naphthalene | 1.0 g | 182-185° C. | 11 h |
| 11 | D-1057-148 | 1,2-Dichlorobenzene | 1.0 g | 175-178° C. | 24 h |
| 12 | D-1057-153 | 1,2-Dichlorobenzene | 5 g | 182-185° C. Microwave | 7 h |

-continued

| S. No. | Lot # | Solvent | Amount | Temp. | Time |
|---|---|---|---|---|---|
| 13 | D-1057-155 | Tetrahydro-naphthalene | 50 g | 182-185° C. Microwave | 4 h |
| 14 | D-1057-172 | Tetrahydro-naphthalene | 308 g | 182-185° C. Microwave | ~7 h |

General Experimental

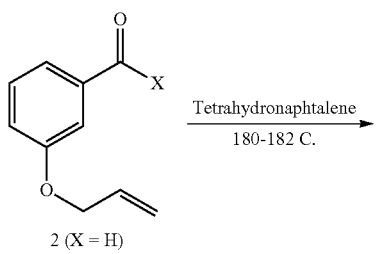

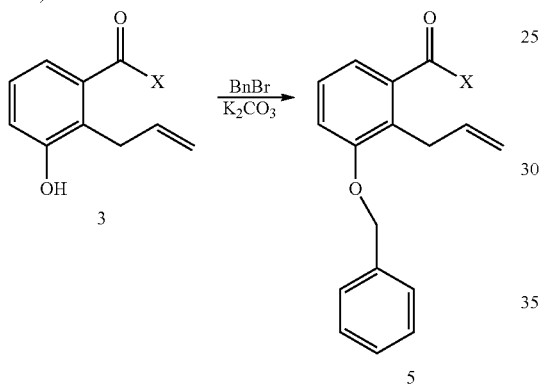

Synthesis of 3-Hydroxy-2-allylbenzaldehyde (8):

Bill of Materials

| Name | MW | Amount | Mole |
|---|---|---|---|
| Allyl ether (7) | NA | 308 g | NA |
| Tetrahydronaphthalene | NA | 300 mL | NA |

To a 3000 ml one neck, round bottom flask equipped with a condenser and thermometer was added allylether (7) (308 g) and tetrahydronaphthalene (300 mL). This reaction mixture was heated slowly up to 180-182° C. (ramped the temp. in 5-10 minutes, internal temperature) in a microwave (power: 1500 Watts) and was kept at this temperature while stirring for 7-8 h. At this stage the reaction mixture turned brown and the reaction mixture was cooled to room temperature followed by cooling at 0 to 5° C. for 30 minutes. The solid was filtered and dried to obtain off-white solid (3-hydroxy-2-allylbenzaldehyde, 8) 145.5 g (47%). The compound (8) was characterized by spectral data. Completion of reaction was monitored by TLC using a thin layer silica gel plate; eluent: 15% ethyl acetate in hexanes.

Synthesis of 2-Allyl-3-benzyloxybenzaldehyde (1):

A 500-mL round-bottom flask equipped with a magnetic stirrer and stir bar was charged with a solution of 3-hydroxy-2-allyl benzaldehyde (8) (25 g in 250 mL acetone), benzyl bromide (28.36 g, 1.05 eq.) and potassium carbonate (54.4 g, 2.5 eq.). The mixture was stirred at room temperature overnight (progress of reaction was monitored by TLC). The suspension was filtered and the filtrate was evaporated in vacuo to afford a crude semi-solid mass. This was taken in 550 ml of hexanes and stirred for 2 h. The solid was crashed out of hexanes and filtered to obtain 2-allyl-3-benzyloxy-benzaldehyde (1), yield 36.6 g (95%). The compound was confirmed by spectral data. Completion of reaction was monitored by TLC using a thin layer silica gel plate; eluent: 20% ethyl acetate in hexanes.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

What is claimed is:

1. A method of producing a compound of formula 3:

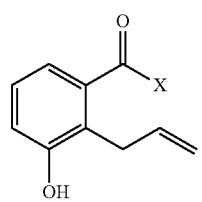

comprising heating a solution comprising a compound of formula 2:

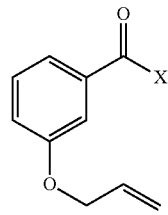

at a temperature ranging from 175° C. to 195° C., wherein said heating comprises irradiating said solution with microwave radiation,
wherein X is $OR^2$,
wherein $R^2$ is $C_{1-4}$ alkyl, unsubstituted or substituted aryl, or unsubstituted or substituted benzyl,
wherein the method further comprises O-alkylating and hydrolyzing the compound of formula 3 to form a compound of formula 11

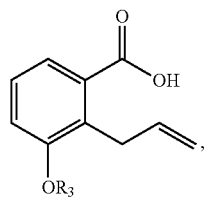

wherein $R_3$ is $C_{1-4}$ alkyl or a phenolic protecting group.

2. The method of claim 1, wherein said solution is heated at the temperature ranging from 182° C. to 185° C.

3. The method of claim 1, wherein the solution further comprises an organic solvent.

4. The method of claim 3, wherein the organic solvent comprises at least one of triglyme, N-methylpyrrolidinone, tetradecane, tetrahydronaphthalene, a mixture of 26.5% diphenyl and 73.5% diphenyl oxide, p-chlorophenol, 1,2-dichlorobenzene, and diphenyl ether.

5. The method of claim 1, wherein $R^2$ is methyl.

6. The method of claim 1, wherein $R^2$ is ethyl.

7. The method of claim 1, further comprising separating the compound of formula 3 from a compound of formula 4:

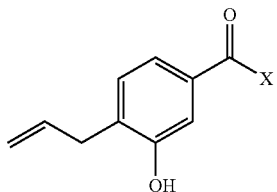

by a selective base hydrolysis.

8. The method of claim 1, further comprising forming from the compound of formula 11 treprostinil using a process comprising Pauson-Khand cyclization.

9. The method of claim 1, wherein $R_3$ is $C_{1-4}$ alkyl.

10. The method of claim 1, wherein $R_3$ is a phenolic protecting group.

11. The method of claim 10, wherein $R_3$ is benzyl.

12. The method of claim 1, further comprising allylating a compound of formula 1

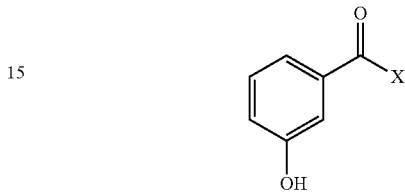

to produce the compound of formula 2.

* * * * *